(12) United States Patent
McDowell, Jr.

(10) Patent No.: US 7,597,910 B2
(45) Date of Patent: Oct. 6, 2009

(54) COMPOSITIONS AND METHODS FOR TREATING PROSTATE DISORDERS

(75) Inventor: John W. McDowell, Jr., Rehoboth, DE (US)

(73) Assignee: SLGM Medical Research Institute, Rehoboth, DE (US)

(*) Notice: Subject to any disclaimer, the term of this patent is extended or adjusted under 35 U.S.C. 154(b) by 171 days.

(21) Appl. No.: 11/207,700

(22) Filed: Aug. 20, 2005

(65) Prior Publication Data
US 2007/0041994 A1 Feb. 22, 2007

(51) Int. Cl.
*A61K 36/00* (2006.01)
*A01N 65/00* (2006.01)
*A61K 36/06* (2006.01)
*A61K 36/09* (2006.01)

(52) U.S. Cl. .................................. 424/725; 424/195.15
(58) Field of Classification Search ........................ None
See application file for complete search history.

(56) References Cited

U.S. PATENT DOCUMENTS

| | | | | |
|---|---|---|---|---|
| 5,071,658 | A | 12/1991 | Fahim | 424/643 |
| 5,543,146 | A | 8/1996 | Perez | 424/195.1 |
| 5,854,404 | A | 12/1998 | Nanba et al. | 532/424 |
| 6,120,825 | A * | 9/2000 | Cirigliano et al. | 426/435 |
| 6,197,309 | B1 | 3/2001 | Wheeler | 424/195.1 |
| 6,261,607 | B1 | 7/2001 | Newmark et al. | 424/727 |
| 6,448,288 | B1 | 9/2002 | Burstein et al. | 514/454 |
| 6,486,204 | B2 | 11/2002 | Waldstreicher et al. | 514/473 |
| 6,582,723 | B2 | 6/2003 | Gorsek | 424/439 |
| 6,616,928 | B1 | 9/2003 | Tazawa et al. | 424/195.15 |
| 6,630,507 | B1 | 10/2003 | Hampson et al. | 514/454 |
| 6,670,392 | B2 | 12/2003 | Fleshner | 514/458 |
| 6,805,866 | B2 | 10/2004 | Keith et al. | 424/195.15 |
| 6,914,072 | B2 | 7/2005 | Burstein et al. | 514/454 |
| 2004/0001856 | A1* | 1/2004 | Jin et al. | 424/195.15 |
| 2004/0049059 | A1* | 3/2004 | Mueller | 549/390 |
| 2005/0008690 | A1* | 1/2005 | Miller | 424/451 |
| 2005/0113327 | A1* | 5/2005 | Roiz et al. | 514/44 |

FOREIGN PATENT DOCUMENTS

| | | |
|---|---|---|
| JP | 2003231644 A * | 8/2003 |
| WO | WO 03011217 A2 * | 2/2003 |

OTHER PUBLICATIONS

Sarfaraz, S.; Afaq, F.; Adhami, V. M.; Mukhtar, H. Cancer Res. 2005; 65(5): 1635-1641.* http://web.archive.org/web/*/http://www.xs4all.nl/~4david/pipe.html (Web Publication Date: Dec. 3, 1998). Date Accessed: Apr. 21, 2006.*
http://web.archive.org/web/*/http://www.marijuana-cannabis-seeds.co.uk/choosing-cannabis-seeds.asp (Web Publication Date: Oct. 20, 2003). Date Accessed: Feb. 2, 2007.*
http://web.archive.org/web/*/http://www.greenmanspage.com/guides/nutrientdisorders.html (Web Publication Date: Feb. 13, 2003). Date Accessed: Feb. 4, 2007.*
Efroymson RA, Sample BE, Suter GW. Environmental toxicology and chemisrtry. 2001; 20 (11): 2561-2571. Abstract only.*
(U1) Wood M. Agricultural Research. 2005. pp. 12-13.*
(V1) Brawley, OW. Reviews in Urology. 2002; 4 (Suppl. 5): S11-S17.*
(W1) http://web.archive.org/web/*/http://www.xs4all.nl/~4david/pipe.html (Web Publication Date: Dec. 3, 1998). Date Accessed: Apr. 21, 2006.*
The American Heritage® Dictionary of the English Language [online] 2000 [Retrieved on Sep. 28, 2007]. Retrieved from the Internet; <http://www.bartleby.com/61/92/E0149200.html>"enhance".*
The American Heritage® Dictionary of the English Language [online] 2000 [Retrieved on Sep. 28, 2007]. Retrieved from the Internet: <http://www.bartleby.com/61/43/E0154300.html> "enrich".*
Bogdanos et al. 'New strategies for the treatment of hormone-independent prostate cancer', Journal of B.U.ON.: Official Journal of the Balkan Union of Oncology, vol. 7, No. 2 (Apr.-Jun. 2002) 107-112, Abstract only.*
Szöke et al. "The possible role of anaerobic bacteria in chronic prostatitis." Int J Androl. vol. 21, No. 3 (Jun. 1998) 163-168, Abstract only.*
(U1) BUPA: Enlarged Prostate [online]Feb. 6, 2004 [Retrieved on Sep. 28, 2007]. Retreived from the Internet: <http://web.archive.org/web/*/http://hcd2.bupa.co.uk/fact_sheets/Mosby_factsheets/BPH.html>.*
(V1) Sarfaraz, S.; Afaq, F.; Adhami, V. M.; Mukhtar, H. Cancer Res. 2005; 65(5): 1635-1641.*

(Continued)

*Primary Examiner*—Christopher R Tate
*Assistant Examiner*—Amy L Clark
(74) *Attorney, Agent, or Firm*—Janet M. Kerr

(57) ABSTRACT

Compositions and methods are described for the treatment of prostatitis, benign prostatic hypertrophy, and prostate cancer. The compositions contain either aqueous extracts or dried mixtures of selenium- and zinc-enriched *cannabis* plant material, shiitake mushrooms, and maitake mushrooms. The compositions are effective in treating prostate disorders by alleviating pain and voiding symptoms, decreasing inflammation and prostate size, reducing cellular proliferation in prostate tissue, and/or reducing PSA levels to within the normal range of 0-4.

16 Claims, No Drawings

OTHER PUBLICATIONS (W1) http://web.archive.org/web/*/http://www.marijuana-cannabis-seeds.co.uk/choosing-cannabis-seeds.asp (Web Publication Date: Oct. 20, 2003). Date Accessed: Feb. 2, 2007.*

(X1) http://web.archive.org/web/*/http://www.greenmanspage.com/guides/nutrientdisorders.html (Web Publication Date: Feb. 13, 2003). Date Accessed: Feb. 4, 2007.*

(U2) Efroymson RA, Sample BE, Suter GW. Environmental toxicology and chemistry. 2001; 20 (11): 2561-2571. Abstract only.*

(V2) Wood M. Agricultural Research. 2005. pp. 12-13.*

(W2) Brawley OW. Reviews in Urology. 2002; 4 (Suppl. 5): S11-S17.*

(X2) "Smokeless Marijuana" [online] Apr. 20, 2003 [Retrived on Sep. 28, 2007]. Retrieved from the Internet: <http://web.archive.org/web/*/http://www.onlinepot.org/medical/smokelesspot.htm>.*

(U3) "New Cannabis Seeds" [online] Jan. 9, 2005 [Retrived on Sep. 28, 2008]. Retrieved from the Internet: <http://web.archive.org/web/*/http://www.planetskunk.com/products_new.php?products_id=75&page=3>.*

(V3) Mushrooms (medicinal): Maitake (*Grifola frondosa*), Reishi (*Ganoderma lucidum*) Shiitake (*Lentinus edodes*). [online]Aug. 4, 2005 [Retrieved on Sep. 28, 2007]. Retrieved from the Internet: <http://www.canceractive.com/page/php?n=n248&style=print>.*

(W3) CANCERactive Issue 4- Oct. 2003 [online] Oct. 2003 [retrieved on Sep. 28, 2008]. Retrieved from the Internet: <http://web.archive.org/web/*/http://www.worldhealth.net/p/aadr-mushrooms-medicinal-maitake-grifola-frondosa--reishi-ganoderma-lucidum-shiitake-lentinus-edodes.html>.*

(X3) Segelman et al. "Cannabis sativa L (Marijuana) IV: Chemical Basis for Increased Potency Related to Novel Method of Preparation", J Pharm Sci, vol. 62, No. 12 (Dec. 1973) 2044-2046.*

(U4) Ruiz et al. "$\Delta$-Tetrahydrocannabinol induces apoptosis in human prostate PC-3 cells via receptor-dependent mechanism". FEBS Letters, vol. 485 (1999) 400-404.*

(V4) Cannabis Nutrient Disorders. Internet Archive Date: Feb. 13, 2003 <Retrieved from the Internet on: Aug. 21, 2009>. Retrieved from: <http://web.archive.org/web/20030213000839/http://www.greenmanspage.com/guides/nutrientdisorders/html>.*

(W4) Johnson, Graham. "A Tea of Pot". Sunday Mirror, Dec. 15, 2002 <Retrieved from the Internet on: Aug. 21, 2008>. Retrieved from http://findarticles.com/p/articles/mi_qn4161/is_20021215/ai_n12855888.*

Ruiz et al., "$\Delta^9$-Tetrahydrocannabinol Induces Apoptosis in Human Prostate PC-3 cells Via a Receptor Independent Mechanism.," FEBS Letters 458:400-404 (1999).

Burstein, S. H., "The Cannabinoid Acids: Nonpshychoactive Derivatives with Therapeutic Potential", Pharmacol. Ther. 82(1):87-96(1999).

Ruiz - Llorente et al., "Expression of Functionally Active Cannabinoid Receptor CB in the Human Prostate Gland", The Prostate 54:95-102 (2003).

Kristal et al., "Vitamin and Mineral Supplement Use Is Associated With Reduced Risk of Prostate Cancer", Cancer Epidemiology, Biomarkers & Prevention, 8: 887-892 (1999).

Thomas, J.A., "Diet, Micronutrients, and the Prostate Gland", Nutrition Reviews 7 (4) : 95-103 (1999).

Kue et al., "Essential Role for G Proteins in Prostate Cancer Cell Growth and Signaling", J. Urol., 164: 2162-2167 (2000).

Galve-Repech et al., "Anti-tumoral action of cannabinoids : Involvement of Sustained Ceramide Accumulation and Extracellular Signal-Regulated Kinase Activation.", Nature MED. 6(3): 313-314 (2000).

Internet Website Address http://dictionary.reference.com/browse/finely accessed Jan. 25, 2009.

* cited by examiner

COMPOSITIONS AND METHODS FOR TREATING PROSTATE DISORDERS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

FIELD OF THE INVENTION

The present invention relates to compositions and methods of using the compositions for the treatment of prostatic disorders in men. More specifically, the invention relates to compositions comprising ingredients having anti-inflammatory, antioxidant, and antitumorigenic activities, and methods of using these compositions to reduce the incidence of or to treat prostatitis, benign prostatic hyperplasia (BPH), and adenocarcinoma of the prostate.

BACKGROUND OF THE INVENTION

The prostate is a gland of the male reproductive system that is located in front of the rectum and just below the bladder. The prostate, comprised largely of muscular and glandular tissue, is wrapped around the urethra, which carries urine from the bladder out through the tip of the penis. The primary function of the prostate is to produce fluid for semen that transports sperm. During the male orgasm, muscular contractions squeeze the prostate's fluid propelling sperm and seminal fluid into the urethra; the sperm and seminal fluid leave the penis during ejaculation.

Disorders of the prostate are fairly common during the aging process and include prostatitis, benign prostatic hyperplasia (BPH), and adenoma of the prostate, or prostate cancer. Prostatitis, which may or may not be the result of an infection, is generally defined as an inflammation of the prostate. Symptoms associated with prostatitis are pain, voiding symptoms such as nocturia, frequency and urgency of urination, incomplete voiding, and decreased force and/or intermittency of the urinary stream, impotence, and infertility. The cause of non-infection related prostatitis is unknown, and therefore, is difficult to treat. Successful treatment of acute bacterial prostatitis and chronic bacterial prostatitis with antibiotics is well established. Inflammatory chronic pelvic pain syndrome is generally treated with antibiotics and anti-inflammatory agents. Alpha blockers can be prescribed to relax muscle tension in the prostate and improve urinary flow. However, alpha blockers are expensive, need to be taken indefinitely in high doses, may have significant side effects, and do not cure the underlying problem or prevent recurrences. Ameliorating the discomfort caused by prostatitis with anti-inflammatory agents or hot sitz baths can be beneficial, but these treatments are temporary and do not cure the disease.

Benign prostatic hyperplasia (BPH) is a noncancerous enlargement of the prostate and is common in men over age 40. Symptoms associated with BPH are similar to those observed with prostatitis. The etiology of BPH is unknown, but may involve hormonal changes associated with aging. With age, testosterone is converted into dihydroxytestosterone (DHT) at higher levels within the prostate via the enzyme, 5-alpha-reductase. DHT binds to androgen receptors, stimulating growth of the prostate. This growth can eventually lead to progressive restriction or obstruction of urine outflow. Incomplete bladder emptying causes stasis and predisposes to infection with secondary inflammatory changes in the bladder. Treatment is directed toward reducing prostate size, stabilizing renal function, eradicating infection, and discontinuing drugs that may induce obstruction. The most widely used drug therapy has been systemic administration of an alpha blocker. Administration of a 5-alpha-reductase inhibitor, which decreases the conversion of testosterone to DHT, has also been used. These drugs can have undesirable side effects of postural hypotension, impotence, and decreased libido. Surgery is the most definitive therapy, and the most widely used surgical procedure is transurethral resection of the prostate. However, approximately 5 to 10% of patients experience some post surgical problems including impotence and incontinence.

Prostate cancer, i.e., adenocarcinoma of the prostate, is the most common malignancy in men greater than 50 years in the US. The incidence increases with each decade of life. Prostate cancer is generally slowly progressive and may cause no symptoms. In late disease, symptoms of bladder outlet obstruction, urethral obstruction, and hematuria may appear and metastasis to the bone may occur. One of the most common means of monitoring for prostate cancer is the routine analysis of serum prostate-specific antigen (PSA). PSA is currently the most sensitive marker for monitoring prostate cancer progression and response to therapy. It has been established that increased PSA levels above the normal range of 0-4 may be indicative of prostate cancer, although elevated levels have been detected in men suffering from prostatitis or BPH. Current traditional treatment regimens for prostate cancer range from minimally invasive treatments, such as watchful waiting, which requires observation of cancer for signs of progression, to major surgery. Treatment regimens such as radiation therapy and cryotherapy eradicate cancer cells but pose risks such as incontinence and impotence. Similarly, treatments directed to decreasing testosterone production or blocking the action of androgens, i.e., anti-hormone therapy, may result in hot flashes or impotence. Radical prostatectomy or surgical removal of the prostate, and radiation therapy are the most common treatment methods for prostate carcinoma. However, radical prostatectomy often results in impotence and urinary incontinence. Similarly, radiation therapy has also been known to produce impotence, incontinence, cystitis, and proctitis. Immunotherapy, i.e., providing agents that stimulate or boost the immune response is currently under investigation. Therapeutic modalities can include any one of, or a combination of, surgery, radiotherapy, cryotherapy, or hormone therapy depending on the stage of the cancer.

No single cause of prostate cancer has been identified. However, associations between risk factors, both nutritional and non-nutritional, and disorders of the prostate have been noted. The major known non-nutritional risk factors for prostate cancer are age, race and family history. With regard to nutritional risk factors, epidemiological studies have shown a possible link between high fat diets and prostate cancer (Thomas, J. A., Nutr. Rev. 57(4):95-103, 1999). In particular, diets that consist of high levels of red meat and dairy products have been correlated with an increase in the risk of advanced prostate cancer. It has also been shown that reducing dietary fat intake can reduce circulating levels of testosterone and other hormones that are known to fuel the growth of prostate cancer cells.

Alterations in the concentration of certain micronutrients in blood and prostate tissue have also been noted. For example, a strong association between low serum selenium levels and an increased incidence of prostate cancer has been reported. Selenium is essential for glutathione peroxidase activity, an enzyme that protects cells from oxidative damage. Results from in vitro studies indicate growth suppression of prostate cancer cells with addition of selenium; this growth suppression has been correlated with cell cycle arrest (Wilkinson, S. and Chodak, G. W., J. Clin. Oncol. 21(11): 2199-2210, 2003). In addition, selenium compounds appear to inhibit tumorigenesis in a number of experimental model systems and in human supplementation studies, leading to a reduction in cancer risk. These studies suggest that selenium compounds act as cancer chemopreventive agents.

Pharmaceutical, nutraceutical, and phytoceutical compositions comprising selenium in combination with one or more ingredients having antiproliferative, anti-inflammatory, and immunostimulating properties for the purpose of maintaining prostate health and treating or preventing prostate cancer have been described. Newmark et al. (U.S. Pat. No. 6,261,607) disclose a phytoceutical composition comprising a number of herbal extracts and selenium. The composition contains phytochemicals having antioxidant and anti-inflammatory activities and is used for promoting prostate health. Fleshner (U.S. Pat. No. 6,670,392) discloses a nutraceutical composition comprising vitamin E and selenium. The composition exhibits enhanced anticarcinogenic properties especially for preventing or treating prostate carcinoma. Waldstreicher et al. (U.S. Pat. No. 6,486,204) disclose a pharmaceutical composition comprising selenium and a cyclooxygenase-2 (COX-2) selective inhibiting drug. COX-2 is a key enzyme in the conversion of arachidonic acid to prostaglandins and other eicosanoids and is expressed in prostate cancer. The composition is used in treating or preventing prostate cancer.

Clinical studies have also shown lower concentrations of zinc in prostate tissue and plasma in persons with prostate cancer compared to controls. Zinc is a component of many physiologically active proteins that play a role in regulating apoptosis, transcription, and cellular differentiation. Based on a population-based, case-control study, Kristal et al. (Cancer Epidemiology, Biomarkers & Prevention, 8:887-892, 1999) determined that zinc supplementation reduced the risk of prostate cancer among participants using zinc daily and therefore exerts a protective effect on prostate health. Fahim (U.S. Pat. No. 5,071,658) discloses an improvement in prostatitis with intraprostatic injections of zinc at a concentration sufficient to increase the amount of prostatic antibacterial factor and to inhibit the rate of prostatic growth. Perez (U.S. Pat. No. 5,543,146) discloses a phytoceutical dietary supplement for alleviating the symptoms associated with enlargement and inflammation of the prostate comprising herbal extracts and zinc. Wheeler (U.S. Pat. No. 6,197,309) discloses a prostate formula with antioxidant, anti-inflammatory, and immunity booster properties comprising herbal extracts, zinc, and selenium.

The immunopotentiating activities and therapeutic effectiveness of polysaccharides obtained from shiitake (*Lentinus edodes*) and maitake (*Grifola*) mushrooms are known in the art. Gorsek (U.S. Pat. No. 6,582,723) discloses an enzymatic extract of Shiitake mushrooms for treating cancer by boosting the immune system and helping the regression of metastases. Nanba et al. (U.S. Pat. No. 5,854,404) discloses an antitumor substance with high immunopotentiating activity. The substance is a polysaccharide isolated from *Grifola*. Keith et al. (U.S. Pat. No. 6,805,866) disclose a composition of mushrooms that has immunoenhancing properties. These properties have been associated with polysaccharides such as alpha glucans, which are in high concentrations in shiitake mushrooms, and beta glucans that are in high concentrations in maitake mushrooms. Tazawa et al. (U.S. Pat. No. 6,616,928) disclose a composition comprising extracts of maitake mushrooms. The composition has immunopotentiating as well as oxygen-scavenging activities that inhibit tumor development.

The medicinal value of *cannabis* has been known for centuries and there has been no evidence of toxicity associated with the medicinal use of *cannabis*. *Cannabis* contains over 400 cannabinoid compounds and produces a wide spectrum of central and peripheral effects including alterations in cognition and memory, analgesic, anticonvulsive, and anti-inflammatory activities, and alleviation of intraocular pressure, nausea, and pain. It has also been demonstrated that cannabinoids have direct antitumor activity as well as immune response-associated antitumor activity. The antitumor activities involve different physiological pathways. For example, cannabinoids signal apoptosis by a pathway involving cannabinoid receptors, sustained ceramide accumulation, and Raf1/extracellular signal-regulated kinase activation (Galve-Roperh, I., et al., Nature Medicine, 6(3):313-319, 2000). Burstein et al. (U.S. Pat. Nos. 6,448,288 and 6,914,072) describe non-psychoactive derivatives of delta-9-THC derivatives which are effective in decreasing cell proliferation in a number of human cancer cell lines including the prostate cancer cell lines DU-145 and PC-3.

The psychotropic principle of *cannabis* is delta-9-tetrahydrocannabinol (delta-9-THC), however, numerous medicinal properties of *cannabis* are thought to be associated with the acid metabolites of delta-9-THC, which show little or no psychoactivity. The physiological effects of the cannabinoids have been attributed to both receptor-mediated and non-receptor-mediated activities. Two types of cannabinoid receptors, CB1 and CB2, have been cloned in humans. The central cannabinoid receptor, CB1, is predominantly located in the central nervous system, although CB1 has also been detected in the gastrointestinal tract and other peripheral tissues. The CB2 receptor is predominantly found in the immune system. These receptors are members of the G-protein-coupled receptor superfamily (Pertwee, R. G., Pharmacol. Ther., 74(2): 129-180, 1997). CB1 and CB2 receptors have been demonstrated in prostate tissue. Recently, Ruiz-Llorente et al. (The Prostate, 54:95-102, 2003) have provided evidence that the CB1 receptor is functionally active in the human prostate gland.

Several reports in the literature demonstrate potential antitumorigenic effects of cannabinoids on prostate tissue and cells via different physiological pathways. For example, Purohit et al. (Endocrinology, 107:848-850, 1980) have established that delta-9-THC inhibits specific binding of dihydroxytestosterone to the androgen receptor in the prostate gland, potentially regulating the serum levels of many sex hormones, thereby having an indirect antitumorigenic effect. Melck et al. (Endocrinology, 141:118-126, 2000) have shown that endocannabinoids, i.e. naturally occurring cannabinoids, inhibit prolactin-induced proliferation in the prostate cell line, DU-145, by inhibiting expression of prolactin receptors via a CB1-dependent mechanism. Ruiz et al. (FEBS Letters, 458:400-404, 1999) have shown that delta-9-THC causes apoptosis in the prostate cell line, PC-3. The apoptotic effect was similar to that apoptotic effect typically associated with ceramide accumulation. Ceramide has been implicated as an important second messenger regulating cell death. In prostate cells, ceramide has been shown to mediate apoptosis.

The analgesic and anti-inflammatory properties of delta-9-THC may be due to its acid metabolites (Burstein, S. H., Pharmacol. Ther., 82(1):87-96, 1999). Acid metabolites may result in an inhibition of eicosanoid synthesis; eicosanoids are mediators of inflammation. It has been postulated that the analgesic and anti-inflammatory properties are due to cannabinoid acids impacting on the arachidonic acid cascade by either causing an accumulation of free arachidonic acid or by inhibiting the synthesis of COX-2. COX-2 products are associated with inflammation. As a potential analgesic and anti-inflammatory therapeutic, it is of interest that chronic users of *cannabis* who are exposed to high blood levels of the delta-9-THC metabolite, delta-8-THC-11-oic acid, appear to be free from non-steroidal anti-inflammatory drug-type toxicity. This may be due in part to a selective inhibition of COX-2.

The prior art indicates that pharmaceuticals, phytochemicals, and nutraceuticals are available for treating disorders of the prostate by providing antioxidant activity, anti-inflammatory activity, and/or antitumorigenic activity. However, it is a concern that pharmaceuticals are expensive, have undesirable side effects, and generally require systemic application. It is a further concern that phytochemicals or extracts obtained from various plant sources can potentially contain toxins, may not be standardized, or may interact with other medications. Therefore, it would be advantageous to provide natural compositions for treatment of prostate disorders that lack toxic properties and that contain desirable therapeutically effective activities such as anti-inflammatory, antioxidant, as well as antitumorigenic activities. In this regard, extracts of *cannabis* plant material have been established to be non-toxic, and to have anti-inflammatory, antioxidant, and antitumorigenic properties in prostate tissue. Given the lack of toxicity of cannabinoids and the ability of the cannabinoids to protect prostate health by a myriad of distinct receptor-mediated and receptor-independent pathways by providing antioxidant protection, altering the conversion of testosterone to dihydroxytestosterone, inhibiting the binding of dihydroxytestosterone to androgen receptors, inducing apoptosis, and decreasing cellular proliferation, compositions containing *cannabis* extracts provide a therapeutically effective means of treating prostate disorders in patients in need thereof.

BRIEF SUMMARY OF THE INVENTION

The primary object of the invention is to provide a composition which is effective in treating prostate disorders.

It is also an object of the invention to provide a composition comprising all natural ingredients with no adverse side effects, the composition and which is effective in treating prostate disorders.

It is further an object of the invention to provide a method of treating prostate disorders comprising administering to a patient in need thereof a composition which is effective in treating prostate disorders.

In a preferred embodiment, the composition comprises a therapeutically effective amount of enhanced *cannabis*. Enhanced *cannabis* is defined as a selenium- and zinc-enriched multigenerational *Cannabis indica*×*Cannabis ruderalis* hybrid plant.

In a second preferred embodiment, the composition comprises a therapeutically effective amount of enhanced *cannabis*, shiitake mushrooms, and maitake mushrooms.

In a preferred embodiment, the method of treating prostate disorders comprises administering to a patient in need thereof a therapeutically effective amount of enhanced *cannabis*. The mode of administration can be by inhalation.

In a second preferred embodiment, the method of treating prostate disorders comprises administering to a patient in need thereof a therapeutically effective amount of a composition comprising and aqueous extract of enhanced *cannabis*, shiitake mushrooms, and maitake mushrooms. The method comprises administration of the composition to mucosal membranes of the urethra or to mucosal membranes of the rectum.

In another preferred embodiment, the method comprises administration of a composition comprising an equal amount of dried enhanced *cannabis*, dried shiitake mushrooms, and dried maitake mushrooms. The composition is encapsulated in a cellulose capsule and administered orally.

The objects of the invention have been obtained by the inventor's discovery that systemic administration of the compositions by oral or inhalation means, or by local administration of the composition to mucosal membranes of the urethra or rectum, is effective in treating prostate disorders.

It is to be understood that the foregoing description is exemplary and explanatory only and not to be viewed as being restrictive of the invention as claimed.

BRIEF DESCRIPTION OF THE SEVERAL VIEWS OF THE DRAWINGS

Not Applicable

DETAILED DESCRIPTION OF THE INVENTION

The present invention provides compositions and methods for the treatment of prostate disorders in patients in need thereof. As used herein, "prostate disorders" refers to prostatitis, benign prostatic hypertrophy, and prostate cancer. "Therapeutically effective amount" of the composition(s) includes but is not limited to an amount of the composition which is effective in treating prostate disorders by alleviating pain and voiding symptoms, decreasing inflammation and prostate size, reducing cellular proliferation in prostate tissue, and/or reducing PSA levels to within the normal range of 0-4.

The enhanced *cannabis* plant is a multigenerational clone developed from an initial crossing of two subspecies of *cannabis*, i.e., *Cannabis indica* and *Cannabis ruderalis* and subsequent clonal propagation. *Cannabis indica* naturally synthesizes high levels of delta-9-THC and is relatively short in height. *Cannabis ruderalis* contains trace levels of delta-9-THC, is relatively short in height, and has a fast growth period. The advantageous properties of the multigenerational clonal cross of *Cannabis indica*×*Cannabis ruderalis* are that the plant produces high concentrations of delta-9-THC, and the plant takes less time to mature. The short stature of the plant enables cultivation indoors allowing for growth in a controlled environment with respect to purified air and water, temperature, and lighting, thereby allowing natural standardization of the types and concentrations of therapeutically effective cannabinoids in the enhanced *cannabis* plant and compositions made therefrom.

It has been established that selenium and zinc are effective nutraceuticals in maintaining prostate health. As *cannabis* plants are known to be accumulators of trace metals, it is advantageous to supplement the plants, particularly at the flowering phase of growth, with an application of a mixture of sea kelp and sea bird guano; this mixture contains organically chelated selenium and zinc. The plants are capable of absorbing and accumulating these minerals during this growth period. A subsequent augmentation with a solution containing chelated zinc during the stage of metabolic maturation allows for maximal accumulation of zinc. At harvest, buds are removed and the stems and leaves and dried in the dark for 2 days, sealed in airtight bags and fresh frozen to keep the selenium- and zinc-enriched *Cannabis indica*×*Cannabis ruderalis* plant material fresh indefinitely.

Methods of interbreeding subspecies of *cannabis* plants for clonal propagation and methods of indoor cultivation are well known in the art (see, for example, Marijuana Grower's Guide, Deluxe Edition by Mel Frank, Red Eye Press, L.A., Calif. and Indoor Marijuana Horticulture; The Medical, Legal, Cultivation Encyclopedia for 2001 and Beyond by Jorge Cervantes).

In a preferred embodiment, the composition of the present invention comprises an aqueous extract of leaves and female buds of an enhanced *cannabis* plant. One gram of dried enhanced *cannabis* is finely chopped and placed in one quart of water which has been purified by a pre-filter, carbon filter, and reverse osmosis filter. One shiitake mushroom (*Lentinula edodes*) and approximately an equal amount by weight of maitake mushroom (*Grifola frondosa*) are chopped, and the chopped mushrooms are added to the quart of purified water. The combination of finely chopped dried *cannabis* and chopped mushrooms forms a suspension in the purified water. The suspension is heated under a light source at a temperature ranging from 95° F. to 105° F. for a period of approximately one to two weeks. The plant and fungal materials are strained from the solution thereby obtaining a particulate-free aqueous extract which is suitable for administration.

The aqueous extract of the present invention may be administered to the mucosal membranes of the urethra by insertion of a small gauge pediatric catheter. Gentle inflation of the distal bulb of the catheter affects occlusion of the urethra and affords a direct route via the central channel of the catheter to the urethra. Infusion of the urethra with the therapeutic solution is readily performed by retrograde injection of the solution through the tip of the catheter. Contact is maintained with the urethra by clamping the catheter to prevent the therapeutic solution from refluxing through the bore of the catheter and by the inflated catheter bulb preventing the solution from draining down the urethra. The sphincter of the bladder prevents spillage of the solution into the bladder. The catheter bulb is deflated at the end of the treatment period and the catheter is removed. Alternatively, the solution can be applied to the prostate via mucosal tissue of the rectum by use of an enema bag or squeeze applicator inserted into the rectum. Delivery of a recommended dosage of 8 fluid ounces of the aqueous solution to the prostate via the mucosal tissues of the urethra or rectum is accomplished twice a day, once in the morning and once in the evening. For prostatitis or BPH, treatment continues until the patient is asymptomatic. For prostate cancer, treatment is continued until the cancer is no longer detectable as determined by means well known in the art.

Local administration of the aqueous composition can be combined with systemic administration of a composition containing dried enhanced *cannabis*. Systemic administration is via inhalation of approximately 0.3 grams of dried enhanced *cannabis* through a water-filled smoking device 3 times daily, preferably before meals. For prostatitis or BPH, treatment continues until the patient is asymptomatic. For prostate cancer, treatment is continued until the cancer is no longer detectable as determined by means well known in the art.

A second composition of the invention is formulated for oral administration. The composition contains three components, dried enhanced *cannabis*, dried shiitake mushrooms and dried maitake mushrooms. Each component is finely ground and a mixture containing approximately 0.3 grams of each component is added to a cellulose capsule. One cellulose capsule is taken in the morning and once in the evening for maximum absorption. For prostatitis or BPH, treatment continues until the patient is asymptomatic. For prostate cancer, treatment is continued until the cancer is no longer detectable as determined by means well known in the art.

All publications and patent documents referenced in this application are incorporated herein by reference in their entirety.

Those skilled in the art will recognize, or be able to ascertain using no more than routine experimentation, many equivalents to the specific embodiments of the invention specifically described herein. Such equivalents are intended to be encompassed in the scope of the following claims.

I claim:

1. A composition for treating prostatitis, benign prostatic hypertrophy, or prostate cancer, wherein the composition comprises a therapeutically effective amount of an aqueous extract of finely chopped dried selenium- and zinc-enhanced *cannabis* (*Cannabis indica*×*Cannabis ruderalis*), chopped shiitake mushrooms (*Lentinula edodes*), and chopped maitake mushrooms (*Grifola frondosa*).

2. The composition of claim 1 wherein said aqueous extract is produced by
   a) mixing in one quart of purified water one gram of finely chopped dried selenium- and zinc-enhanced *cannabis* (*Cannabis indica*×*Cannabis ruderalis*), one chopped shiitake mushroom (*Lentinula edodes*), and chopped maitake mushrooms (*Grifola frondosa*) in an amount equivalent by weight to the chopped shiitake mushroom (*Lentinula edodes*) to form a suspension;
   b) heating the suspension at a temperature range of approximately 95° F. to 105° F. for a period of one to two weeks; and
   c) straining the heated suspension to obtain said aqueous extract.

3. A composition for treating prostate cancer, the composition comprising a therapeutically effective amount of a mixture of three components, wherein the three components are finely ground dried selenium- and zinc-enriched *cannabis* (*Cannabis indica*×*Cannabis ruderalis*), finely ground dried shiitake mushrooms (*Lentinula edodes*), and finely ground maitake mushrooms (*Grifola frondosa*).

4. The composition of claim 3 wherein the three components of the mixture are present in equal amounts.

5. The composition of claim 4, wherein 0.3 grams of each component is present in the mixture.

6. The composition of claim 4 wherein the composition is packaged in a cellulose capsule suitable for oral administration.

7. The composition of claim 5 wherein the composition is packaged in a cellulose capsule for oral administration.

8. A method of treating prostatitis, benign prostatic hypertrophy, or prostate cancer in a patient in need thereof, said method comprising administering a therapeutically effective amount of a composition comprising selenium- and zinc-enhanced *cannabis* (*Cannabis indica*×*Cannabis ruderalis*), shiitake mushrooms (*Lentinula edodes*), and maitake mushrooms (*Grifola frondosa*); or an aqueous extract thereof.

9. The method of claim 8, wherein the composition is an aqueous extract of finely chopped dried selenium- and zinc-enhanced *cannabis* (*Cannabis indica*×*Cannabis ruderalis*), chopped shiitake mushrooms (*Lentinula edodes*), and chopped maitake mushrooms (*Grifola frondosa*).

10. A method of treating prostatitis, benign prostatic hypertrophy, or prostate cancer in a patient in need thereof, said method comprising administering a therapeutically effective amount of the composition of claim 2.

11. The method of claim 10, wherein the therapeutically effective amount is 8 fluid ounces.

12. The method of claim 11, wherein the composition is administered twice daily.

13. The method of claim 12, wherein the composition is administered to the mucosal membranes of the urethra by way of a pediatric catheter.

14. The method of claim 12, wherein the composition is administered to the mucosal membranes of the rectum by way of an enema or squeeze applicator.

15. A method of treating prostatitis, benign prostatic hypertrophy, or prostate cancer in a patient in need thereof, said method comprising administering the composition of claim 5.

16. The method of claim 15, wherein the composition is administered twice daily.

* * * * *